(12) United States Patent
Blais et al.

(10) Patent No.: US 8,212,098 B2
(45) Date of Patent: Jul. 3, 2012

(54) HF ALKYLATION PROCESS WITH INTERNAL ACID REGENERATION

(75) Inventors: D'Arcy H. J. Blais, Toronto (CA); Doug F. Bodeux, Beaumont (CA); Steve L. Burgwin, Pickering (CA); Alexander D. Chan, Edmonton (CA); Gary S. Locke, Sarnia (CA); Jerry H. Squires, Edmonton (CA); Sarah J. Virtue, Toronto (CA)

(73) Assignee: ExxonMobil Research & Engineering Company, Annandale, NJ (US)

( * ) Notice: Subject to any disclaimer, the term of this patent is extended or adjusted under 35 U.S.C. 154(b) by 1212 days.

(21) Appl. No.: 12/007,301

(22) Filed: Jan. 9, 2008

(65) Prior Publication Data

US 2008/0177123 A1    Jul. 24, 2008

Related U.S. Application Data

(60) Provisional application No. 60/880,950, filed on Jan. 18, 2007.

(51) Int. Cl.
*C07C 2/62* (2006.01)
(52) U.S. Cl. ........ 585/719; 585/709; 585/718; 585/721; 585/723
(58) Field of Classification Search .................. 585/723, 585/709, 718, 719, 721; 422/600
See application file for complete search history.

(56) References Cited

U.S. PATENT DOCUMENTS

| | | | | |
|---|---|---|---|---|
| 3,478,125 A | * | 11/1969 | Chapman | 585/719 |
| 3,993,706 A | * | 11/1976 | Mikulicz et al. | 585/710 |
| 4,192,825 A | * | 3/1980 | Chapman | 585/719 |
| 4,373,110 A | * | 2/1983 | Hutson, Jr. | 585/719 |
| 4,404,418 A | * | 9/1983 | Hutson et al. | 585/710 |
| 4,454,369 A | * | 6/1984 | Hutson et al. | 585/719 |
| 4,470,879 A | * | 9/1984 | Hutson, Jr. | 203/3 |
| 4,663,026 A | * | 5/1987 | Louie et al. | 208/262.1 |
| 5,382,746 A | * | 1/1995 | Child et al. | 585/802 |
| 5,767,335 A | * | 6/1998 | Anderson et al. | 585/723 |
| 6,552,241 B1 | * | 4/2003 | Randolph et al. | 585/719 |

* cited by examiner

*Primary Examiner* — In Suk Bullock
*Assistant Examiner* — Bradley Etherton
(74) *Attorney, Agent, or Firm* — Malcolm D. Keen; Glenn T. Barrett

(57) ABSTRACT

An improved process for removing polymeric by-product (ASO) from the HF alkylation acid in an HF alkylation unit used for the production of gasoline boiling range alkylate product by olefin/iso-paraffin alkylation, comprises fractionating a portion of the circulating HF alkylation acid inventory of the unit with a portion of hot alkylate product in a fractionation zone to from an overhead product comprising HF alkylation acid and water and a bottoms fraction comprising the polymeric by-product and alkylate. The bottoms fraction is sent to the isoparaffin stripper of the unit to remove trace HF alkylation acid as overhead and form a product stream of hot alkylate as a bottoms fraction.

3 Claims, 1 Drawing Sheet

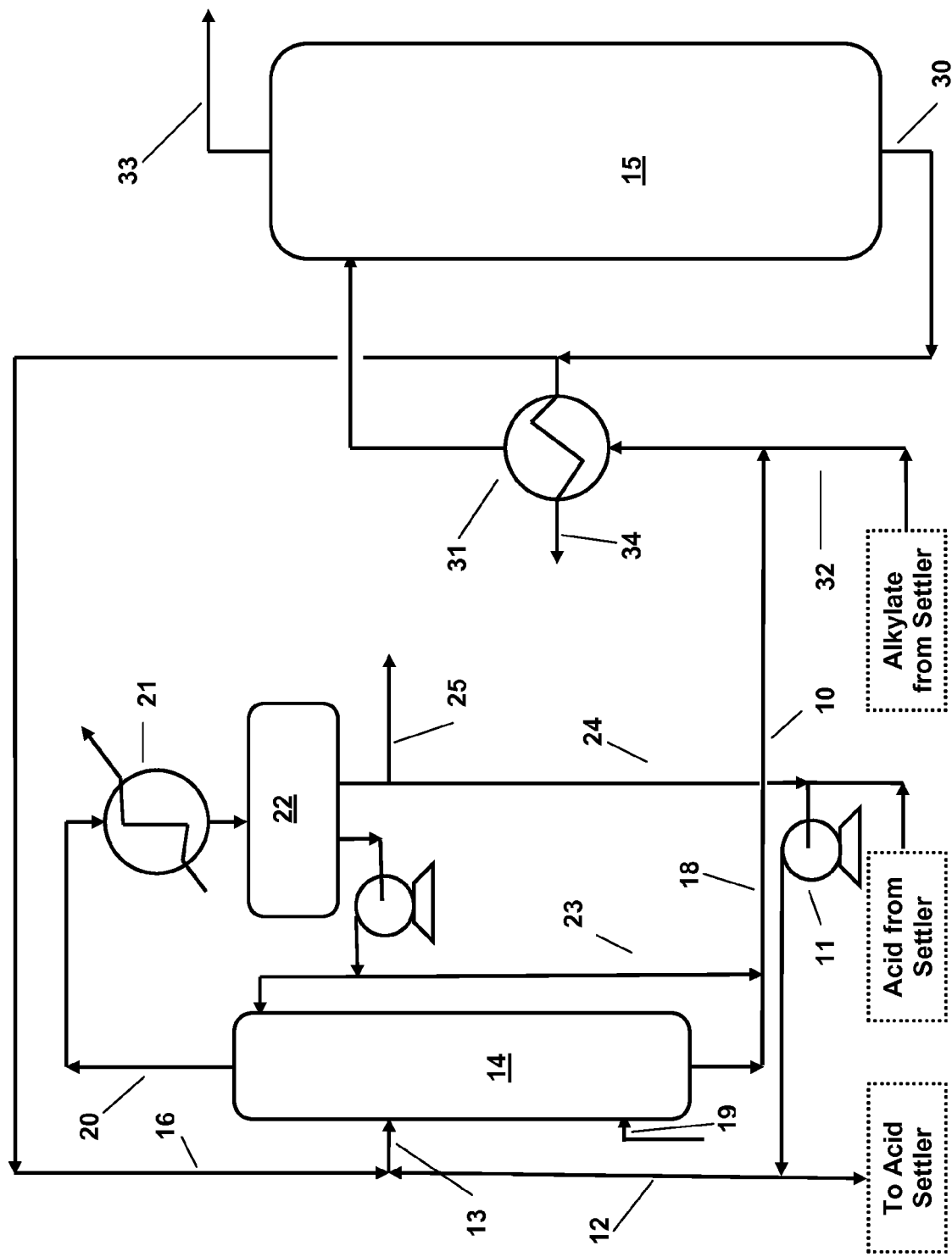

HF ALKYLATION PROCESS WITH INTERNAL ACID REGENERATION

CROSS REFERENCE TO RELATED APPLICATIONS

This application claims priority from U.S. Provisional Application No. 60/880,950, filed 18 Jan. 2007, entitled "HF Alkylation Process with Internal Acid Regeneration".

FIELD OF THE INVENTION

This invention relates to iso-paraffin/olefin alkylation and more particularly, to hydrofluoric acid (HF) alkylation. In this specification, the term "alkylation" will be used to refer to the iso-paraffin/olefin alkylation process used to make gasoline blend components useful in aviation and motor gasolines and "HF alkylation" to this process using hydrofluoric acid as the catalyst.

BACKGROUND OF THE INVENTION

The iso-paraffin/olefin alkylation process is widely used to manufacture a high octane quality blend component for aviation and motor gasoline which is also valued for its relatively low vapor pressure, low sensitivity and, because of its freedom from aromatic components, its environmental acceptability. The process typically reacts a $C_2$ to $C_5$ olefin with isobutane in the presence of an acidic catalyst to produce the alkylate product.

Hydrofluoric and sulfuric acid alkylation processes share inherent drawbacks including environmental and safety concerns, acid consumption, and sludge disposal but in spite of efforts to develop an inherently safe alkylation process, both processes have achieved widespread utilization with the HF process being noted for producing a higher quality product with more favorable unit economics. Although hydrogen fluoride, or hydrofluoric acid (HF) is highly toxic and corrosive, extensive experience in its use in the refinery have shown that it can be handled safely, provided the hazards are recognized and precautions taken. The HF alkylation process is described in general terms in *Modern Petroleum Technology*, Hobson et al (Ed), Applied Science Publishers Ltd. 1973, ISBN 085334 487 6. A survey of HF alkylation may be found in *Handbook of Petroleum Refining Processes*, Meyers, R. A. (Ed.), McGraw-Hill Professional Publishing, 2nd edition (Aug. 1, 1996), ISBN: 0070417962.

In order to improve the operation of the HF alkylation process as well as the economics of the process it is desirable to regenerate the HF alkylation acid by removing the polymeric by-product which forms during the alkylation reactions; this polymer, comprising polymers of differing degrees of conjugation, is frequently referred to as "acid soluble oil" (ASO) since it is miscible with the HF acid phase. Removal of the ASO is necessary to preserve the concentration of the acid at the high level desirable for good alkylation performance while removal of water is required in order to reduce corrosion within the unit as well as to maintain product octane quality. Normally, the acid concentration is maintained at 88 to 94 weight percent by the continuous or periodic addition of fresh acid and withdrawal of spent acid with the water content kept in the range of 0.5 to 1.0 percent.

One previously used method for removing the polymer from the acid inventory is by internal regeneration. A small amount of acid (with polymer and trace water) is injected into the isostripper feed line with the large amount of alkylate and butanes feeding the tower. The acid flashes overhead and the polymer leaves with the alkylate via the bottom of the tower. There is, however, a limit on the amount of the acid in the hydrocarbon feed to the isostripper: major corrosion problems in the isostripper overhead may occur with excess acid in the isostripper feed. Excess acid can also result in a separate acid phase in the downstream isoparaffin recycle circuit where it mixes with olefin feed, resulting in accelerated corrosion in the tower.

When removal of water is the objective, as it is on a fairly frequent schedule, external regeneration is necessary. In the external regeneration method, a small amount of acid (with polymer and trace water) is injected into a separate distillation column, which is operated in batch mode with isoparaffin used as a heating and stripping medium. The tower separates dry acid overhead and a mixture of HF acid, water and polymer leaves as a bottoms fraction. The mixture is neutralized, and the aqueous phase is separated from polymer through a series of separator drums. This method results in loss of HF acid and costly use of neutralization chemicals. It is also manually intensive.

An external regeneration method of this type is described in U.S. Pat. No. 5,547,909 (Carlson). In this method, the acid phase from the settler is removed and a portion is routed to a separator column which enables the polymer (ASO) to be separated from the HF of the acid phase. Cooled isoparaffin is used as column reflux and heat is supplied by means of isoparaffin introduced as stripping medium at the foot of the column. Acid, free of ASO and water is removed as overhead and is recirculated to the settler. A portion of the bottoms fraction is recycled to a higher level in the tower, possibly to make the separation more effective. While this technique may be capable of improving on the conventional external separation by attempting to get closer to an azeotropic mixture of water, acid and polymer in the bottom of the tower, (acid content of the bottoms stream about 40-50%), it still fails to achieve a satisfactory level of acid recovery and significant losses of acid can be expected. Another external HF acid regeneration scheme is proposed in U.S. Pat. No. 6,228,650 (Moore et al) using an improved control scheme to monitor and control process operation but again, since the same basic regeneration scheme is used in which the heat is supplied solely by the iso-paraffin used for stripping, the acid regeneration remains at a level which is less than optimal. A method of stripping the HF from the alkylation acid using hydrogen is proposed in U.S. Pat. No. 5,461,183 (Del Rossi et al) but this method, requiring external hydrogen is not well suited to incorporation within the non-hydrogenative HF alkylation unit.

There are therefore deficiencies in both methods of regeneration: internal regeneration in the isostripper removes polymer but is ineffective for removal of water to the low levels required in the process while external regeneration, by contrast, is required for the removal of water but results in an uneconomic loss of HF acid if the water content is to be maintained at the appropriate level. Given that the process economics favor internal regeneration, it would be desirable to improve the operation of that practice even if it were not completely effective at removal of water.

We have now devised a method of HF acid regeneration which enables the polymer to be separated from almost all of the acid, together with water, leaving the polymer ASO with only trace acid in the alkylate product as a bottoms fraction. The method we have devised operates by using the heat from a stream of hot alkylate to strip the acid, together with trace levels of water, from a slipstream of alkylation acid with its polymer (and trace water) in an acid treating tower (fractionation tower) in which the acid and water are vaporized as overhead, leaving the polymer behind as a bottoms fraction which leaves the tower with recycled alkylate. This polymer-laden alkylate is injected into the isostripper feed to remove any trace residual acid as isostripper overhead. The HF acid, water and light hydrocarbon vapors from the treating tower are condensed into an overhead receiver drum, where light hydrocarbon is separated from the acid phase. The remaining acid and trace water is virtually polymer free and can be returned to the circulating acid system or fed to an external regeneration unit for removal of water, when required. The acid treating tower allows for elimination of internal regeneration as well as a reduction in external regeneration. In addition, since the acid treating tower configuration sends only acid (and trace water) to the external regeneration unit, the costs associated with extensive handling of polymer in external regeneration are eliminated. Because water and acid are largely removed in the acid treating tower, the problems of isostripper overhead corrosion from excess acid are largely eliminated.

SUMMARY OF THE INVENTION

According to the present invention, an improved process for removing polymeric by-product (ASO) from the HF alkylation acid in an HF alkylation unit used for the production of gasoline boiling range alkylate product by olefin/iso-paraffin alkylation, comprises fractionating a portion of the circulating HF alkylation acid inventory of the unit with a portion of hot alkylate product in a fractionation zone to from an overhead product comprising HF alkylation acid and water and a bottoms fraction comprising the polymeric by-product and alkylate. The bottoms fraction is sent to the isoparaffin stripper of the unit to remove trace HF alkylation acid as overhead and form a product stream of hot alkylate as a bottoms fraction.

In its essentials, the HF alkylation unit incorporating this recovery system comprises:
(i) an alkylation reactor with its associated acid settler having an upper outlet for alkylate product and a lower outlet for HF alkylation acid,
(ii) an isostripper for separating isoparaffin from alkylate product from the settler by fractionation to produce an isoparaffin overhead stream at an overhead outlet and an alkylate product stream as a bottoms fraction at a lower outlet, the isostripper having an inlet connected to the upper outlet of the settler,
(iii) a fractionator tower having an inlet connected to the lower outlet of the settler to receive a slipstream portion of the HF alkylation acid from the acid circuit,
(iv) an inlet connected to the lower outlet of the isostripper to receive a slipstream portion of the alkylate bottoms stream from the isostripper.

The isostripper is also fitted with an overhead outlet for fractionated HF alkylation acid and trace water and a bottoms outlet for alkylate product and polymeric by-product ASO, the bottoms outlet being connected to the inlet of the isostripper to provide the hot alkylate for the fractionation zone as well as allowing for withdrawal of the alkylate product stream which is taken to the recovery and purification section.

DRAWINGS

The single FIGURE of the accompanying drawings is a simplified process schematic of an acid recovery section of an HF alkylation unit with its associated equipment.

DETAILED DESCRIPTION

The FIGURE shows the acid recovery section of a complete HF alkylation unit which, in addition to the components shown, includes the conventional reaction section with its reactor and feed lines and acid settler in which the hydrocarbon phase including alkylate product is allowed to separate under gravity from the denser acid phase. The settler, in the conventional manner, has an inlet from the reactor (not shown) as well as an upper outlet for the alkylate product and a lower outlet for the HF alkylation acid which circulates in the alkylation acid circuit in the conventional way, except for the slipstream taken to the acid regeneration/recovery section described below.

The acid feed to the acid regeneration/recovery section comprises a slipstream of acid from the lower (acid) outlet of the settler; this slipstream enters the treating section through line 10 and is circulated by means of circulation pump 11 which forms part of the alkylation acid circuit. A slipstream of acid passes through line 12 to the acid inlet 13 of acid treater tower 14 along with hot alkylate from isostripper 15, entering the acid treater tower by way of line 16. In the tower, which operates as a fractionation zone, the hot alkylate from the isostripper provides heat for flashing the acid which leaves the tower along with a trace of water as overhead through line 20. Additional heat to the fractionation tower may be providing by reboil of the bottoms fraction leaving through line 18 with the reboil entering through line 19. Alternatively, hot iso-paraffin vapor from the isostripper may be conducted from the isostripper to line 19 to add heat at this level and provide the necessary level of vapor traffic for proper tower operation. Normally, the use of hot alkylate injection is preferred provided that a sufficiently hot stream of acid-free isoparaffin is available since the reboil service requirements are quite stringent in this application.

In the ratios injected into the tower, the acid and alkylate remain as two immiscible phases and as the acid vaporizes in the tower, the polymer becomes a separate phase on its own, leaving the tower through line 18 to pass to isostripper 15 in which the polymer will become fully dissolved in the larger volume of hot alkylate and iso-paraffin. The presence of two separate phases is acceptable in this relatively small tower in which the acid and water from the slipstream are separated from the alkylate and polymer.

The overhead from the fractionation tower comprising acid plus trace water along with any light hydrocarbon entrained in the settler and any iso-paraffin introduced into the tower as stripping medium passes through line 20 to cooler 21 and then to receiver drum 22 in which the hydrocarbon phase is separated from the acid phase with the hydrocarbon being returned as reflux and by way of line 23 to the isostripper. The drum is provided with some form of oil/acid separation capability, such as an overflow weir or other separation device. The acid from the overhead receiver is returned through line 24 to the acid circuit by means of acid circulation pump 11. When water removal from acid is required, this acid stream can be rerouted to an external acid regenerator (not shown) by way of line 25. Since it contains no polymer, the azeotropic mixture can be neutralized and disposed of virtually free of polymer handling problems.

The bottoms fraction from tower 14 comprising alkylate, polymer and light hydrocarbon from receiver drum 22, is passed to isostripper 15 and enters the isostripper (itself a fractionator) at a level downstream of the preheat exchanger since, without the need for internal acid regeneration, a high level of acid solubility is present to maintain the bottoms stream trace acid in solution. The isostripper separates out the alkylate as bottoms, leaving the isostripper through line 30 and passing to the product recovery section (not shown) through line 34 via heat exchanger 31 which provides heat for the incoming alkylate-containing stream from the settler in line 32; the slipstream of hot alkylate from the isostripper is taken out into line 16 to the treater tower as described above. Isoparaffin passes out through line 33.

The acid treatment tower and associated equipment which comes into contact with the acid-containing streams must be built of acid-resistant alloy materials such as Monel™ metal, since the acid phase can be more corrosive when heated. This, however, is economically favorable compared to the use of corrosion-resistant alloys in the isostripper overhead which is a larger item of equipment. The acid treatment tower operates at a higher temperature than the isostripper so that the composition of the overhead can approach azeotropic in a way that is not possible in the isostripper. The number of stages of separation required in the tower will be dependent on the desired degree of separation between hydrocarbon (alkylate+ polymer) and acid. In the simplest case, a flash drum can be used, which will send more hydrocarbon overhead. Alternatively, a refluxed tower with many stages minimizes the amount of hydrocarbon going overhead. In either case, some butane and light alkylate will end up condensing in the overhead receiver-drum. Because this fraction will contain dissolved acid, it will need to be reinjected back into the isostripper tower via line 23 for removal of the acid at that point.

The remainder of the HF alkylation process including identities and feed hydrocarbons, temperatures and equipment items can be conventional in type. The olefin feed will typically be $C_2$-$C_4$ olefins with preference being given to butylenes although propylene and ethylene may also be used with corresponding changes in product properties and in the appropriate process conditions, as is known. The isoparaffin most favored for use in the HF alkylation process is isobutane. The alkylate product may be treated in the conventional way in the product recovery and purification section, e.g. by caustic neutralization to form the desired gasoline blend component.

The process may be operated with a vapor suppressant additive to improve safety margins in the event of an uncontrolled acid release from the unit. The vapor suppressant additives normally contemplated are those which reduce the volatility of the HF acid. Compounds of this type which have been proposed include organic sulfones, ammonia, amines such as the lower alkylamines (methyl to pentyl), pyridine, alkylpyridines, picoline, melamine, hexmethylenetetramine. A number of different sulfones have been proposed for this purpose but the one generally preferred is sulfolane (tetramethylenesulfone) with 3-methylsulfolane and 24-dimethylsulfolane also being suitable. A more detailed description of vapor suppressant additives of this type is given in U.S. Pat. No. 6,114,593 to which reference is made for this description. When a vapor suppressant additive is used the process is often referred to as modified HF alkylation (MHF).

The invention claimed is:

1. A process for removing polymeric by-product ASO (acid soluble oil) from the circulating HF alkylation acid in an HF alkylation unit used for the production of gasoline boiling range alkylate product by alkylation of an isoparaffin with an olefin, which comprises:

alkylating an isoparaffin with an olefin in the presence of HF alkylation catalyst in an alkylation reactor, subjecting the HF alkylation reaction product from the reactor to separation in an acid settler from which a stream comprising a portion of the HF alkylation acid containing ASO is withdrawn, mixing the withdrawn HF alkylation acid stream with a portion of hot alkylate product from an isoparaffin stripper of the unit, fractionating the withdrawn HF alkylation acid stream in a fractionation zone having vertically spaced lower and upper ends with the lower end maintained at a higher temperature than the upper end by heat supplied to the lower end by external reboil of a bottoms stream obtained from the lower end, to form an overhead product comprising HF alkylation acid and water and a bottoms fraction comprising the polymeric by-product and alkylate and fractionating the resulting bottoms fraction in the isoparaffin stripper of the unit to remove trace HF alkylation acid as overhead and form a stream of hot alkylate product and polymeric by-product as a bottoms fraction in the isoparaffin stripper.

2. A process according to claim 1 in which HF alkylation acid and water in the overhead of the fractionation zone also comprises light hydrocarbon and the HF alkylation acid and water in this overhead are separated from the light hydrocarbon and sent to the HF alkylation acid circulating in the unit.

3. A process according to claim 2 in which the light hydrocarbon separated from the HF alkylation acid is sent to the isoparaffin stripper with the alkylate product.

* * * * *